United States Patent [19]
Robert

[11] 4,208,427
[45] Jun. 17, 1980

[54] PREVENTING ENTEROPOOLING INDUCED DIARRHEA BY PROSTACYCLIN OR 11-OXO-PROSTAGLANDIN ADMINISTRATION

[75] Inventor: Andre Robert, Kalamazoo, Mich.

[73] Assignee: The Upjohn Company, Kalamazoo, Mich.

[21] Appl. No.: 614

[22] Filed: Jan. 2, 1979

Related U.S. Application Data

[63] Continuation of Ser. No. 905,330, May 12, 1978, abandoned.

[51] Int. Cl.$^2$ .................... A61K 31/19; A61K 31/34; A61K 31/215; A61K 31/275

[52] U.S. Cl. .................... 424/285; 424/304; 424/305; 424/317

[58] Field of Search ............... 424/285, 305, 317, 304

[56] References Cited

PUBLICATIONS

Schaaf et al., Chem. Abst., vol. 80 (1974), p. 145,554v.

*Primary Examiner*—Stanley J. Friedman
*Attorney, Agent, or Firm*—Robert A. Armitage

[57] ABSTRACT

The present invention relates to a method for the prophylaxis and treatment of the diarrheogenic effects of enteropooling inducers by administration of an anti-enteropooling dose of an 11-oxo-prostaglandin or a prostacyclin.

10 Claims, No Drawings

PREVENTING ENTEROPOOLING INDUCED DIARRHEA BY PROSTACYCLIN OR 11-OXO-PROSTAGLANDIN ADMINISTRATION

This is a continuation of application Ser. No. 905,330, filed May 12, 1978 now abandoned.

BACKGROUND OF THE INVENTION

Numerous agents, such as diarrheogenic prostaglandins, various parasitic oranisms, and toxins produced by microbial agents, are known in the art to have a recognized diarrheogenic potential in mammals. One measure of the potential for the induction of diarrhea for a given agent is its ability to cause the accumulation of fluid in the small intestine of standard laboratory animals treated with or exposed to the agent. This phenomena of fluid accumulation, referred to as enteropooling, is quantitatively determined by methods known in the art. See, for example, Robert, A., et al., Prostaglandins, 11:809–828 (1976). Agents which can cause enteropooling at a level sufficient to cause diarrhea are referred to herein as enteropooling inducers.

One such class of enteropooling inducers, the diarrheogenic prostaglandins, are members of a family of naturally-occurring fatty acids (such as $PGE_2$ and $PGF_2\alpha$), and include various chemical analogs thereof known in the art. Among these prostaglandin analogs known in the art there are the PGC-type compounds of U.S. Pat. No. 3,993,686, the 9-deoxy-9-methylene-PGF-type compounds of U.S. Pat. Nos. 4,021,467 and 4,060,534; the 11-deoxy-PG-type compounds of U.S. Pat. Nos. 4,029,693 and 3,987,072; the $8\beta$, $12\alpha$-PG-type compounds of U.S. Pat. No. 3,979,483; the 2,2-difluoro-PG-type compounds of U.S. Pat. Nos. 4,001,300; the cis-4,5-didehydro-PG-type compounds of U.S. Pat. Nos. 4,032,561 and 3,933,889; the inter-phenylene-PG-type compounds of U.S. Pat. Nos. 4,020,097 and 3,997,566; the 5,6-didehydro-$PG_2$-type or 4,4,5,5-tetradehydro-$PG_1$-type compounds of U.S. Pat. No. 4,013,695; the 5-oxa-$PG_1$-type compounds of U.S. Pat. Nos. 3,931,279 and 3,864,387; the 4-oxa-$PG_1$-type and 3-oxa-$PG_1$-type compounds of U.S. Pat. No. 3,944,593; the 13-cis-PG-type compounds of U.S. Pat. No. 4,026,909; the 13,14-didehydro-PG-type compounds of U.S. Pat. Nos. 4,029,681 and 4,018,803; the $\omega$-aryl-PG-type compounds of U.S. Pat. No. 3,987,087; the $\omega$-aryloxy-PG-type compounds of U.S. Pat. No. 3,864,387; the 16-alkyl-PG-type compounds of U.S. Pat. No. 3,903,131; the 16-fluoro-PG-type compounds of U.S. Pat. No. 3,962,293; the 15-methyl-PG-type compounds of U.S. Pat. No. 3,728,382.

While the naturally-occurring prostaglandins are carboxylic acids, numerous derivatives thereof are known in the art. For example, ester derivatives, including especially aromatic and phenacyl esters, are known in the art. See U.S. Pat. Nos. 3,069,032, 3,598,858, 3,979,440, and 3,984,062. Likewise, salts of these carboxylic acids are known in the art. See U.S. Pat. Nos. 3,069,332 and 3,958,858 cited above, as well as other references such as U.S. Pat. Nos. 3,657,327 and 3,888,916. Other derivatives of the prostaglandins, such as the amides thereof, are known in the art. See U.S. Pat. Nos. 3,853,941, 3,884,942, 3,903,299, 3,880,883, and 3,953,470.

Finally, there are also known macrocyclic lactone derivatives of the prostaglandins as is, for example, described by Corey, E. J., et al., JACS 97:653 (1975) and U.S. Pat. Nos. 3,931,206, 4,067,991, 4,049,648, 4,032,543, 4,045,449, and 4,049,678.

In addition to these various carbonyl-containing prostaglandin analogs, there are likewise known in the art acidic, non-carboxylic prostaglandin analogs such as tetrazoles and sulfonates. See for example the 2-decarboxycarboxy-2-tetrazolyl-PG analogs described in U.S. Pat. Nos. 3,883,513, 3,932,389, 3,984,400, and 4,035,360. Also 2-decarboxy-2-sulfonyl-type compounds are described in U.S. Pat. No. 3,922,301.

Among the various other modifications at the C-2 position of the known prostaglandin analogs is the replacement of the carboxyl with an amine, as is for example described in U.S. Pat. No. 4,073,808 and Derwent Farmdoc CPI No. 46957V (abstracting Belgian Pat. No. 849,963).

Numerous references also describe primary alcohols corresponding to the known prostaglandins and analogs thereof as are described in U.S. Pat. Nos. 4,028,419, 4,055,602, 4,032,576, 3,931,207, 3,878,239, 3,966,792, 4,024,174, 3,962,312, 3,636,120, 3,723,528, 3,895,058, 3,954,881, 4,004,021, and 3,962,218. In addition to these 2-decarboxy-2-hydroxymethyl-PG compounds, there are known the corresponding C-2 aldehydes as described in U.S. Pat. Nos. 3,931,296 and 3,953,435. See also Derwent Farmdoc CPI No. 35953X and at 93049X for a description of further 2-decarboxy-2-carboxaldehyde-PG analogs. Finally, the C-2 acetals thereof are described at Derwent Farmdoc CPI No. 94924X.

There are further known in the art 11-oxo-prostaglandins, notably PGD-type, $9\beta$-PGD-type, 9-deoxy-PGD-type, 9-deoxy-9,10-didehydro-PGD-type, and the corresponding 12,13-didehydro analogs thereof. These 11-oxo-prostaglandins are described in U.S. Pat. No. 4,016,184.

In addition to the various prostaglandins, including prostaglandin analogs and 11-oxo-prostaglandins known to the art, there are further known the prostacyclins. As that term is used herein, the term prostacyclins refers not only to prostacyclin or $PGI_2$ itself, but various, and notably more stable, analogs thereof.

Prostacyclin is an unsaturated heterocyclic carboxylic acid and its preparation and certain of its pharmacological uses are described in Belgian Pat. No. 851,122 (published as Derwent Farmdoc CPI No. 57511Y) and Belgian Pat. No. 854,463 (published as Derwent Farmdoc CPI No. 81213Y). Among the analogs of prostacyclin are the 5,6-dihydro-$PGI_1$ compounds, described in Belgian Pat. No. 855,224 (published as Derwent Farmdoc CPI No. 86540Y); the 9-thia analog of prostacyclin, described at JACS 99:7734 (1977); the 4,5-didehydro-$PGI_1$ compounds, described at JCS Chem. Comm. 1977:331–332 and JACS 99:2006–2008 (1977) and U.S. Pat. No. 4,109,082, filed on an even date herewith; the C-9 nitrogen analogs of prostacyclin, described in U.S. Pat. No. 4,097,489; the 5-hydroxy-$PGI_1$ compounds, described in U.S. Pat. No. 4,110,532 the 4-oxo-$PGI_1$ compounds, described in U.S. Pat. No. 4,126,744 the 7,8-didehydro-$PGI_1$ compounds, described in U.S. Pat. No. 4,151,351, the 6,7-didehydro-$PGI_1$ compounds, described in U.S. Pat. No. 4,128,713 the carbocyclic analogs of prostacyclin, described in German Offenlegungschrift 2,329,092, the C-5 isomers of prostacyclin, described in U.S. Pat. No. 4,150,222, the 9-deoxy-9-epoxymethylene-$PGI_1$ compounds, described in U.S. Pat. No. 4,130,569, and the 7a-homo-$PGI_1$ compounds, described in U.S. Ser. No. 260,518, now abandoned.

SUMMARY OF THE INVENTION

The present invention relates to a novel method for the pharmacologic use of prostacyclins and 11-oxo-prostaglandins.

The present invention further provides a method whereby the undesirable diarrheogenic effects of enteropooling inducers are minimized or eliminated.

The present invention particularly provides:

a method of preventing or ameliorating diarrhea in a mammal susceptible to diarrhea development by virtue of exposure to or challenge with an enteropooling inducer, or eliminating or reducing diarrhea in a mammal suffereing therefrom, which comprises:

administering an anti-enteropooling systemic dose of a prostacyclin or 11-oxo-prostaglandin.

In accordance with the present method an enteropooling inducer is defined as any agent which causes the accumulation of fluid in the intestines sufficient to result in diarrhea on the expulsion of such fluid. Enteropooling inducers include the diarrheogenic prostaglandins, various parasitic organisms, toxins produced by certain microbial agents, radiation, certain pancreatic diseases, certain surgical procedures (e.g., vagatomy), and other, but uncharacterized agents (e.g., idiopathic enteropooling inducers.

Diarrheogenic prostaglandins are known in the art as useful pharmacological agents for a wide variety of purposes. In particular, diarrheogenic prostaglandins are known to be useful for obstetric and gynecological purposes, including abortion, menstrual regulation, and labor induction. Further, certain of the prostaglandins (particularly the PGE-type compound) are useful in lowering mammalian blood pressure. Other pharmacological effects of the diarrheogenic prostaglandin include reduction of gastric secretion (facilitating healing of gastric and duodenal ulcers), blood platelet aggregation inhibition (reducing the possibility of thrombosis), and brohchodilation (e.g. antiasthmatic uses). For examples of the numerous pharmacological effects induced by the diarrheogenic prostaglandins, see the various references provided above describing various prostaglandins, including their analogs.

A further characteristic of the diarrheogenic prostaglandins is their ability to stimulate smooth muscle, notably gastrointestinal smooth muscle. Further, the diarrheogenic prostaglandins, while exhibiting one or more of the highly desirable pharmacological activity above, cause enteropooling or the collection of substantial quantities of fluid in the intestine. This accumulation of fluid in the intestine, together with the stimulation of gastrointestinal smooth muscle which causes fluid transit in the gastrointestinal tract, is responsible for the diarrhea, especially watery diarrhea, associated with diarrheogenic prostaglandin administration in many patients.

For the purposes of the present invention, diarrheogenic prostaglandins are therefore those prostaglandins which cause diarrhea in the rat at therapeutic doses as a result of their potency in the rat enteropooling assay described in Robert, A., et al., Prostaglandins 11:809–828 (1967). Accordingly, the diarrheogenic prostaglandins include prostaglandins such as $PGE_2$, $PGA_1$, $PGA_2$, and $PGB_2$; as well as analogs such as 16, 16-dimethyl-$PGE_2$, 15-methyl-$PGE_2$, 15-epi-15-methyl-$PGE_2$, 15-methyl-$PGE_2\beta$, and 15-epi-15-methyl-$PGF_2\beta$. In accordance with this definition of diarrheogenic prostaglandins, the compounds so defined are those which, when administered to humans or valuable domestic animals at therapeutic doses, cause diarrhea as a side effect of the administration thereof.

In addition to the diarrheogenic prostaglandins, other examples of enteropooling inducers include the toxins produced by certain microbial agents. One notable example of a toxin which is an enteropooling inducer is cholera toxin or the toxin produced by *Vibro cholerae*. Further numerous viral pathogens, such as influenza viruses, are also known enteropooling inducers. Likewise, certain parasitic agents in the gastrointestinal tract are known to cause diarrhea by induction of enteropooling.

The improvement of the present invention comprises, as indicated above, the administration of a prostacyclin or an 11-oxo-prostaglandin. As indicated above, the term prostacyclin and the term 11-oxo-prostaglandin refer to compounds whose preparation and formulation for pharmacological purposes is described in the references cited above. For example, these references describe the importance of certain prostacyclins and the 11-oxo-prostaglandins as platelet aggregation inhibitors, thus rendering such compounds potent anti-thrombotic agents. The present invention comprises, however, the further discovery that the 11-oxo-prostaglandins and prostacyclins are further characterized by an ability to inhibit the enteropooling effects of enteropooling-inducers. Accordingly, this further pharmacologic property renders the prostacycins and 11-prostaglandins useful in accordance with the present method.

For the purposes of the present method, any convenient systemic form of administration is employed. See, for example, the routes of administration and dosage regimens described in the above references.

Further with respect to the above method, both prophylactic (i.e., prevention and amelioration) and therapeutic (elimination or reduction) treatment of diarrhea is within the scope of the present invention.

For the therapeutic use, the prostacyclin or 11-oxo-prostaglandin is administered in a dose sufficient to either reduce or eliminate diarrhea.

In the prophylaxis of diarrhea, the prostacyclin or 11-oxo-prostaglandin is administered in anticipation of an exposure to, concomitantly with exposure to, or at the earliest convenience after an exposure to an enteropooling inducer.

The prostacyclin or 11-oxo-prostaglandin is administered at an anti-enteropooling dose in accordance with the present invention. Depending upon the incidence and extent of diarrhea anticipated or actually encountered with the enteropooling inducer, an anti-enteropooling dose of the prostacyclin or 11-oxo-prostaglandin is employed to reduce the amount of fluid anticipated to accumulate or actually accumulating in the intestine from 50 percent ($ED_{50}$) to 100 percent ($ED_{100}$). In determining the amount of prostacyclin or 11-oxo-prostaglandin sufficient to result in the desired diminution of enteropooling, firstly the relative anti-enteropooling potency of the particular prostacyclin or 11-oxo-prostaglandin is determined.

This relative potency is determined by readily available experimental techniques. Accordingly, the rat enteropooling assay as described by A. Robert is undertaken, but with the modification that, although all rats are treated with the control diarrheogenic prostaglandin, a second group is concomitantly treated with either the prostacyclin or 11-oxo-prostaglandin. For convenience, subcutaneous dosages of the prostacyclin or 11-oxo-prostaglandin are given. Further the prostacyclin or 11-oxo-prostaglandin is given about 10 minutes prior to the administration of the control diarrheogenic prostaglandin. By this method the decrease in enteropooling obtained by treatment with the prostacyclin or 11-oxo-prostaglandin is readily determined. Further the reduction in enteropooling in animals treated with the prostacyclin or 11-oxo-prostaglandin will be dose dependent, thus permitting a determination of the $ED_5O$ and $ED_{100}$ values which are used in determining relative potency.

For example, by the procedure described above the anti-enteropooling $ED_{50}$ of prostacyclin (or $PGI_2$) is 15 $\mu g/kg$ subcutaneously when a 100 $\mu g/kg$ oral dose of 16,16-dimethyl-$PGE_2$ (the control diarrheogenic prostaglandin) is administered 10 minutes after treatment with $PGI_2$. Moreover the anti-enteropooling $ED_{50}$ for $PGI_2$ is substantially independent of the dosage of the control diarrheogenic prostaglandin, being an effective inhibitor of enteropooling induced with doses from 0.5–1000 $\mu g/kg$ orally of 16,16-dimethyl-$PGE_2$.

Thus, in accordance with the present invention an anti-enteropooling $ED_{50}$ or $ED_{100}$ is determined for each prostacyclin or 11-oxo-prostaglandin substantially independently of the nature of the enteropooling inducer (e.g., prostacyclin).

Therefore the anti-enteropooling dose in accordance with the present invention is readily determined solely as a function of the relative anti-enteropooling potency of the prostacyclin or 11-oxo-prostaglandin.

In many cases, for example, complete elimination of diarrhea is not a necessary clinical endpoint. Accordingly enteropooling is reduced by less (e.g., 50 percent) than the amount necessary to return the animal or patient to a pattern of normal defecation (e.g., 90 percent reduction in enteropooling), but by at least the amount which the attending physician or veterinarian determines to be the necessary and appropriate clinical endpoint to avoid the untoward effects of massive diarrhea (e.g., dehydration and death). Accordingly the present invention provides for both the total abolition of diarrhea (i.e., prevention or elimination) or the more conservative approach in merely quantitatively reducing diarrhea or fluid loss from undesirably high levels (i.e., amelioration or reduction). As used herein the term anti-enteropooling dose thus includes both concepts of dose sufficient to prevent or eliminate and ameliorate or reduce diarrhea.

Thus, for the purposes of the present invention dosages in the range of 0.1 $\mu g/kg/day$ to 10 $mg/kg/day$ will be efficacious as indicated above, with the exact dose depending upon potency and the route of administration.

The practice of the method according to the present invention further requires the systemic administration of the anti-enteropooling dose of prostacyclin or 11-oxo-prostaglandin. For the purposes of the present invention, systemic administration refers to administration by any conventional route. The attending physician or veterinarian can readily determine the appropriate route of administration by the clinical or veterinary presentation and available knowledge regarding the stability and/or suitability of the prostacyclin or 11-oxo-prostaglandin for administration by a particular route being considered. Thus, for example, for compounds like prostacyclin, which are unstable in acidic media, oral administration is ordinarily avoided. In other instances, ease and simplicity of administration would provide a preference for oral formulation and use of the prostacyclin or 11-oxo-prostaglandin.

Finally, while the present invention relates to an improved method for the induction of prostaglandin-like pharmacological effects with diarrheogenic prostaglandin inmammals, the preferred embodiment of the present invention is its use in man. Other uses of the present method include, however, the use in valuable domestic animals such as cattle and pigs or canine, feline, or equine species.

By another embodiment of the method of the present invention, the anti-enteropooling dose of the prostacyclin or 11-oxo-prostaglandin is administered concurrently with other antidiarrheal agents known in the art. These art antidiarrheal agents include substances which reduce intestinal motility or induce the gelling or solidification of intestinal contents. Thus, for example, antidiarrheal agents employed concurrently with the prostacyclin or 11-oxo-prostaglandin include mixtures of koalin and pectin, atropine, and narcotics (e.g., morphine) or other substances (e.g., diphenoxylate and loperamide).

U.S. Pat. Nos. 4,109,082; 4,097,489; 4,110,532; 4,126,744; 4,151,351; 4,128,713; and 4,150,222 are incorporated here by reference for the description thereof of various prostaglandins.

I claim:

1. A method of preventing or ameliorating diarrhea in a mammal susceptible to diarrhea development by virtue of exposure to or challenge with an enteropooling inducer, or eliminating or reducing diarrhea in a mammal suffering therefrom, which comprises:

administering an anti-enteropooling systemic dose of a prostacyclin or 11-oxo-prostaglandin.

2. A method according to claim 1, wherein said anti-enteropooling dose is the $ED_{50}$.

3. A method according to claim 1, wherein said enteropooling inducer is 16,16-dimethyl-$PGE_2$.

4. A method according to claim 1, wherein said prostacyclin or 11-oxo-prostaglandin is $PGD_2$.

5. A method according to claim 1, wherein said prostacyclin or 11-oxo-prostaglandin is $PGI_2$.

6. A method according to claim 1, wherein said prostacyclin or 11-oxo-prostaglandin is $PGI_1$.

7. A method according to claim 1, wherein diarrhea is prevented or ameliorated.

8. A method according to claim 1, wherein diarrhea is reduced or eliminated.

9. A method according to claim 1, wherein the prostacyclin or 11-oxo-prostaglandin is used concurrently with one or more additional antidiarrheal agents.

10. A method according to claim 2, 7, 8, or 9, wherein said prostacyclin or 11-oxo-prostaglandin is (a) $PGI_1$,
(b) 7,8-didehydro-$PGI_1$,
(c) 6,7-didehydro-$PGI_1$,
(d) 4,5-didehydro-$PGI_1$,
(e) 5-hydroxy-$PGI_1$,
(f) 4-oxo-$PGI_1$,
(g) 7a-homo-$PGI_1$,
(h) 9-thia-$PGI_2$,
(i) 9-deoxy-9α, 6-nitrilo-$PGF_1$, or
(j) $PGI_2$, or a salt or ester thereof.

* * * * *

UNITED STATES PATENT OFFICE
CERTIFICATE OF CORRECTION

Patent No. 4,208,427   Dated 17 June 1980

Inventor(s) Andre Robert

It is certified that error appears in the above-identified patent and that said Letters Patent are hereby corrected as shown below:

Column 1, line 11, "oranisms" should read -- organisms --;
Column 4, line 8, "Vibro cholerae" should read -- Vibrio cholerae --;
line 29, "11-prostaglandins" should read -- 11-oxo-prostaglandins --;
Column 5, line 10, "Ed$_5$0" should read -- ED$_{50}$ --.

Signed and Sealed this

Twenty-first Day of April 1981

[SEAL]

Attest:

RENE D. TEGTMEYER

Attesting Officer    Acting Commissioner of Patents and Trademarks